US00PP20218P3

(12) United States Plant Patent
Hambali

(10) Patent No.: US PP20,218 P3
(45) Date of Patent: Aug. 18, 2009

(54) ***AGLAONEMA* PLANT NAMED 'TWYAG0020'**

(50) Latin Name: *Aglaonema commutatum var. tricolor×rotundum hybrid*
Varietal Denomination: TWYAG0020

(75) Inventor: Gregori Garnadi Hambali, Bogor (ID)

(73) Assignee: Kerry's Bromeliad Nursery, Inc., Apopka, FL (US)

( * ) Notice: Subject to any disclaimer, the term of this patent is extended or adjusted under 35 U.S.C. 154(b) by 70 days.

(21) Appl. No.: 11/894,574

(22) Filed: Aug. 21, 2007

(65) Prior Publication Data

US 2009/0055984 P1 Feb. 26, 2009

(51) Int. Cl.
*A01H 5/00* (2006.01)

(52) U.S. Cl. ..... Plt./376
(58) Field of Classification Search ..... Plt./376
See application file for complete search history.

(56) References Cited

PUBLICATIONS

UPOV Rom GTITM Computer Database, GTI Jouve Retrieval Software Jan. 2008 Citation for 'TWYAG0020'.*

* cited by examiner

*Primary Examiner*—Annette H Para
(74) *Attorney, Agent, or Firm*—Jondle & Associates, P.C.

(57) ABSTRACT

A new *Aglaonema* plant particularly distinguished by having a very dense leafy, compact and upright branched growth habit, being small to intermediate in stature, leaves that are small and uniform, very vigorous, profuse suckering, producing many axillary branches and leaves and having a more rapid growth rate than typical commercial *Aglaonema* cultivars, is disclosed.

1 Drawing Sheet

Genus and species: *Aglaonema commutatum* var. *tricolor×A. rotundum* hybrid.
Variety denomination: 'TWYAG0020'.

BACKGROUND OF THE NEW PLANT

The present invention comprises a new and distinct cultivar of *Aglaonema,* botanically known as *Aglaonema commutatum* var. *tricolor×A. rotundum* hybrid, and hereinafter referred to by the cultivar name 'TWYAG0020'. The present variety originated from a hybridization made in June 2001 in Bogor, Indonesia in a cultivated field between the female parent, an un-named seedling of *Aglaonema commutatum* tricolor (unpatented) and the male parent, an un-named seedling of *Aglaonema rotundum* (unpatented). A single seedling was subsequently found in January 2003 among the progeny and chosen for further asexual propagation.

The new cultivar was created in Bogor, W. Java, Indonesia and has been asexually reproduced repeatedly by vegetative cuttings and sucker division in Apopka, Fla. The present invention has been found to retain its distinctive characteristics through successive asexual propagations.

SUMMARY OF THE INVENTION

The following are the most outstanding and distinguishing characteristics of this new cultivar when grown under normal horticultural practices in Apopka, Fla.

1. Small to intermediate in stature;
2. Leaves are small and uniform;
3. Very densely leafy, compact and upright branched growth habit;
4. Profuse suckering and very vigorous;
5. Produces many axillary branches and leaves; and 6. Has a more rapid growth rate than typical commercial *Aglaonema* cultivars.

DESCRIPTION OF PHOTOGRAPHS

This new *Aglaonema* plant is illustrated by the accompanying photographs which show overall plant habit and leaves. The colors shown are as true as can be reasonably obtained by conventional photographic procedures.

DESCRIPTION OF THE NEW CULTIVAR

Figure 1:
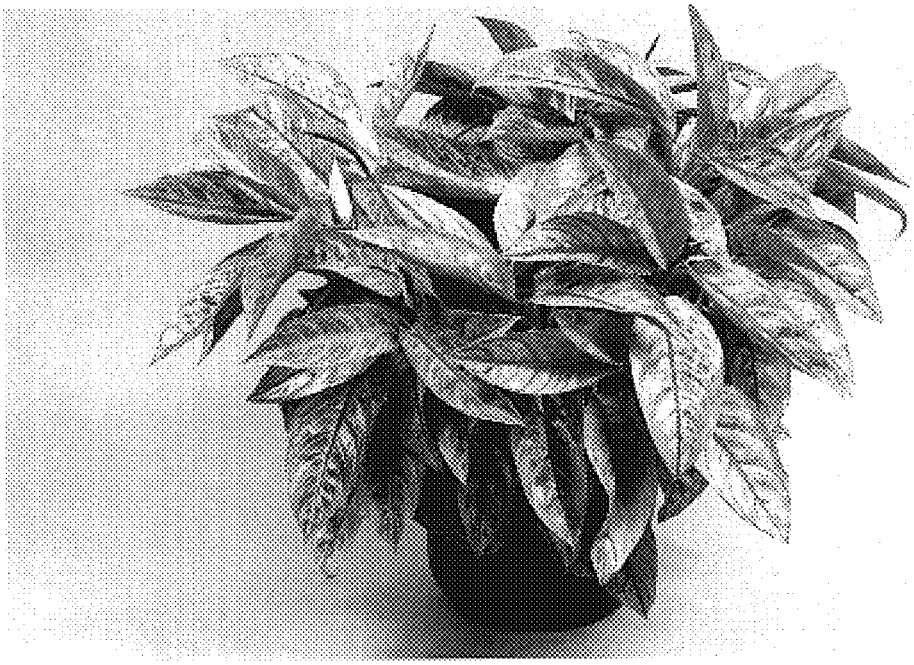
FIG. 1 shows the overall plant habit of the new plant.
Figure 2:
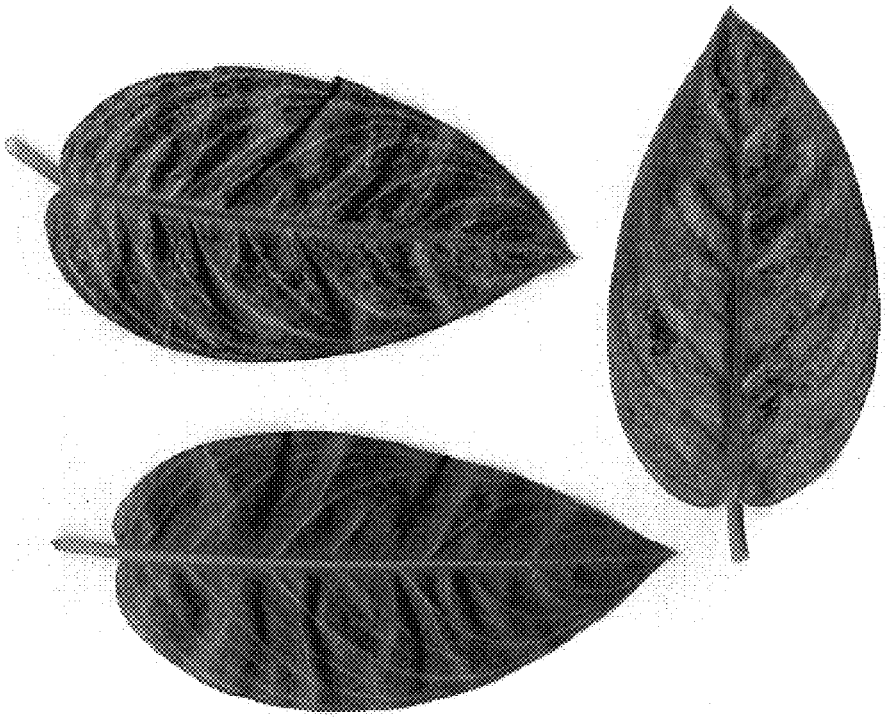
FIG. 2 shows the upper and lower surface of mature leaves.

The following detailed description sets forth the distinctive characteristics of 'TWYAG0020'. The data which define these characteristics were collected from asexual reproductions carried out in Apopka, Fla. The plant history was taken on 16-month-old plants started from a single 4-leaf rooted cutting, still in a vegetative state and grown in Apopka, Fla. Rooted cuttings were planted in 20-cm pots and grown in a greenhouse in May 2006. The average daily temperature was about 85° F. to 95° F. and the average nightly temperature was about 65° F. to 78° F. The light level was about 1500 to 3000 foot candles. The plants were pinched twice. Color readings were taken under natural light. Color references are primarily to the R.H.S. Colour Chart of The Royal Horticultural Society of London (R.H.S.) (2001).

DETAILED BOTANICAL DESCRIPTION

Classification:
*Family.*—*Araceae.*
*Botanical.*—*Aglaonema* hybrid.
*Common name.*—Chinese Evergreen.

Parentage:

*Female parent.*—An un-named seedling of *Aglaonema commutatum tricolor* (unpatented).

*Male parent.*—An un-named seedling of *Aglaonema rotundum* (unpatented).

Growth:

*Form.*—Symmetrical, wider than tall; new leaves held upright, mature leaves arch outward.

*Growth and branching habit.*—Very densely leafy, compact; upright highly branched growth habit (basal branching); small to intermediate in stature.

*Height* (*from soil to top of leaf plane*).—30 cm to 38 cm.

*Diameter* (*area of spread, measured from leaf tip to leaf tip across the canopy*).—46 cm to 50 cm.

*Time to produce a finished plant.*—16 months starting from a single 4-leaf rooted cutting and pinched twice.

*Root description.*—Abundant, fleshy white roots with finer lateral branches.

*Number of divisions or clumps per year.*—About 8 to 10 four-leaf cuttings per year.

*Durability of foliage to stresses.*—Leaves hold up well against damage from shipping and handling; plant is durable, excellent indoor keeping quality.

*High temperature tolerance.*—To about 104° F. for several hours without damage.

*Low temperature tolerance.*—To about 55° F. for several hours without damage.

Stems:

*Number of branches per plant.*—33.

*Length* (*from soil line to the junction of the newest two leaves*).—13 cm.

*Diameter* (*measured from the midpoint*).—0.8 cm.

*Internode length.*—1.0 cm to 1.4 cm.

*Color.*—Immature: RHS 145B to RHS 145C with areas of RHS 157D. Mature: RHS 161D. Oldest stems: RHS 194D with areas of RHS 161C.

*Appearance* (*shape*).—Columnar, cylindrical, upright.

*Aspect.*—Vertical, upright.

*Strength.*—Sturdy, strong, somewhat flexible.

*Axillary buds.*—Shape: Elliptic, flat. Length: 0.4 cm. Width: 0.2 cm. Color: RHS 158D.

Leaves:

*Arrangement.*—Alternate, single, arranged in a spiral along the stem.

*Quantity of leaves per stem.*—8.

*Length.*—11.5 cm to 14.4 cm.

*Width.*—Flattened: 6.8 cm to 7.5 cm. Not flattened: 4.5 cm to 5.6 cm; leaf blade folds upward along the midrib.

*Shape.*—Ovate to elliptic.

*Apex.*—Acute.

*Base.*—Obtuse.

*Margin.*—Smooth, entire, mostly flat with some broad undulations.

*Texture.*—Smooth; new leaves shiny; mature leaves shiny to glossy; the leaf blade is convex between the main veins and somewhat puckered along the midrib giving the leaf a textured appearance.

*Pubescence.*—None.

*Young leaf* (*newly expanded leaf*).—Color: Upper side: RHS 147A base color; RHS 147B to RHS 191A (dark silver-green) areas which follow the primary veins; suffusion of RHS 146D to RHS 150D (yellow-green) spots; areas adjacent to the primary veins and midrib are RHS 150D to RHS 146D variably tinged with RHS 54B. Under side: Base color lighter than, but closest to RHS N186C with a cast of RHS 147A (dark-green), suffused with spots of RHS 185C; areas adjacent to the primary veins and midrib are RHS 185C.

*Mature leaf.*—Color: Upper side: Base color darker than but closest to RHS 147A; RHS 189A (dark silver-green) areas which follow the primary veins; suffusion of RHS 146D to RHS 150D (yellow-green) spots; areas adjacent to the primary veins and midrib are RHS 150D to RHS 146D variably tinged with RHS 53B to RHS 53C. Under side: Base color RHS N186C with a cast of RHS 147A (dark-green), suffused with spots of RHS 185C; areas adjacent to the primary veins and midrib are RHS 185C.

*Venation pattern.*—Pinnate, radiating outward from the midrib in a herringbone arrangement.

*Venation color* (*newly expanded leaf*).—Upper side: Primary veins: RHS 150D to RHS 146D flushed with RHS 53D. Midrib: RHS 53D. Under side: Primary veins: RHS 53D to RHS 185C. Midrib: RHS 54C.

*Venation color* (*mature leaf*).—Upper side: Primary veins: RHS 150D to RHS 146D flushed with RHS 53C to RHS 53D. Midrib: RHS 53C to RHS 53D. Under side: Primary veins: RHS 53D. Midrib: RHS 54C.

Petioles:

*Aspect.*—Vertical upright when newly expanded, becoming curved outward and about 45° with maturity.

*Length.*—8.5 cm.

*Diameter.*—Distal: 0.3 cm. Proximal (petiole and petiole sheath clasps the stem proximally). Flattened: 2.0 cm. Natural diameter: 0.8 cm.

*Color.*—Distal: RHS 49A to RHS 50C (between the top of the wing and the base of the leaf). Proximal: RHS 49B streaked with RHS 49A. Area adjacent to stem: RHS 49D.

*Wing length.*—5.6 cm.

*Wing diameter.*—Mid-point: 0.5 cm. Base: 0.8 cm. Depth: 0.3 cm.

*Wing color.*—Inside: RHS 49D. Outside: RHS 49B streaked and flushed with RHS 49A. Area adjacent to stem: RHS 49D.

Inflorescence: None observed.

Fruit and seed set: None observed.

Disease and insect resistance: Typical of *Aglaonema;* no particular susceptibility or resistance to pests or diseases noted.

COMPARISON WITH KNOWN CULTIVARS

'TWYAG0020' differs from the female parent, a typical *Aglaonema commutatum* var. *tricolor* by having dark-pink petioles, while the female parent has light-pink petioles. 'TWYAG0020' has leaves (upper surface) that are a combination of green, yellow and red colors, while the female parent has leaves (upper surface) that are plain green with silver stripes. In addition, 'TYWAG0020' has profuse suckering, while the female parent has moderate suckering.

'TWYAG0020' differs from the male parent, a typical *A. rotundum* by having leaves that are reddish in color on the lower surface and no red veins on the upper surface, while the male parent has leaves that are dark-purple or maroon in color on the lower surface and have red veins on the upper surface.

'TWYAG0020' differs from the commercial variety 'Red Gold' (unpatented) in that the leaves are a reddish color on the upper surface, while for 'Red Gold' the leaves are a pale yellowish-green color on the upper surface. In addition, 'TWYAG0020' has profuse suckering, while 'Red Gold' has moderate suckering.

'TWYAG0020' differs from the commercial variety 'Key Largo' (U.S. Plant Pat. No. 17,550) in that 'TWYAG0020' has a shorter and narrower growth habit than 'Key Largo'. In addition, 'TWYAG0020' has shorter, narrower leaves with more yellow color in them than 'Key Largo'.

I claim:

1. A new and distinct cultivar of *Aglaonema* plant as shown and described herein.

* * * * *